United States Patent [19]

Li

[11] 4,116,950

[45] Sep. 26, 1978

[54] ANALOGS OF HUMAN β-ENDORPHIN

[75] Inventor: Choh Hao Li, Berkeley, Calif.

[73] Assignee: Hoffmann-La Roche Inc., Nutley, N.J.

[21] Appl. No.: 869,555

[22] Filed: Jan. 16, 1978

[51] Int. Cl.² .................... C07C 103/52; A61K 37/00
[52] U.S. Cl. .............................. 260/112.5 R; 424/177
[58] Field of Search .................. 260/112.5 R; 424/177

[56] References Cited

U.S. PATENT DOCUMENTS 4,038,222   7/1977   Li ................................... 260/112.5 R

Primary Examiner—Delbert R. Phillips
Attorney, Agent, or Firm—Samuel L. Welt; George M. Gould

[57] ABSTRACT

Analogs of human β-endorphin having a phenylalanine at position 27 and glycine at position 31 are disclosed. The subject analogs exhibit potent analgesic activity.

5 Claims, No Drawings

ANALOGS OF HUMAN β-ENDORPHIN

BACKGROUND OF THE INVENTION

The isolation of β-endorphins from mammalian brain and pituitary extracts has been described in the art. See for example Li and Chung, Proc. Natl. Acad. Sci. U.S.A. 73,1145 (1976) and U.S. Pat. No. 4,038,222. The availability of synthetic methods for preparing β-endorphin has allowed studies into structure-activity relationships with analogs of β-endorphin.

Initial modifications have been made in the amino terminal or enkephalin portion of the molecule, i.e., (1–5) β-endorphin. Similar modifications made in enkephalin had produced enkephalin analogs with substantially enhanced analgesic activity over that of the parent compound. However, the β-endorphin analogs, with the exception of [D-Ala$_2$] - β-endorphin, did not have the level of activity of the parent compound. See in this regard U.S. patent application Ser. No. 776,569, filed Mar. 11, 1977 and Yamashiro et al., Int. J. Pept. Prot. Res. 10,159 (1977).

DESCRIPTION OF THE INVENTION

The present invention relates to analogs of human β-endorphin ($β_h$-endorphin) which are substituted in the carboxyl terminus region of the molecule and which may further be substituted in the amino terminus region. More particularly the present invention relates to compounds of the formula

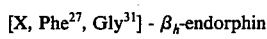

[X, Phe$^{27}$, Gly$^{31}$] - $β_h$-endorphin where X is selected from null, Ala$^{6,7}$, Nle$^5$, and D-Thr$^2$. A most preferred compound of this invention is where X is null, i.e., [Phe$^{27}$, Gly$^{31}$] - $β_h$-endorphin.

The compounds of the invention can be conveniently prepared by utilizing peptide synthesis procedures well known in the art. Preferred procedures useful in preparing the instant compounds involve the solid phase method of Merrifield, J. Am. Chem. Soc. 85, 2149 (1963) particularly as modified by Yamashiro and Li, Proc. Natl. Acad. Sci. U.S.A. 71, 4945 (1974).

In a suitable solid phase synthesis, the carboxy terminus t-butyloxycarbonyl (Boc) protected glycine residue is coupled to a conventional solid phase peptide synthesis resin such as chloromethylated polystyrene crosslinked with 1 to 2% divinyl benzene.

The Boc-glycyl resin is then alternatively subjected to deblocking in 55% trifluoroacetic acid (methylene chloride, neutralizing with diisopropylethylamine and finally coupled with the preformed symmetrical anhydride of the next Boc amino acid in the sequence. After completion of the synthetic cycles with all required amino acids, the final protected peptide resin is treated with liquid HF in a manner known per se to yield the free crude product. Purification is accomplished by chromatography on carboxymethylcellulose followed by partition chromatography on Sephadex G-50.

Characterization of the final product peptides is accomplished by amino acid analysis of acid hydrolysates and enzyme digests, paper electrophoresis and thin layer chromatography.

The compounds of the present invention are potent opiate agonists and thus are useful as analgesics, narcotic antagonists and anti-diarrhea agents.

They can be used as medicaments in the form of pharmaceutical preparations having direct or delayed liberation of the active ingredient which contain them in association with a compatible carrier material. This carrier material can be an organic or inorganic inert carrier material suitable for enteral, precutaneous or parenteral application such as water, gelatin, gum arabic, lactose, starch, magnesium stearate, talc, vegetable oils, polyalkylene-glycols, petroleum jelly, etc. The pharmaceutical preparations can be made up in a solid form (e.g., as tablets, dragees, suppositories or capsules) or in a liquid form (e.g., as solutions, suspensions or emulsions). A preferred form suitable for parenteral administration involves preparation of a purified, lyophilized form of the active compound which is reconstituted prior to use by the addition of sterile, distilled water or saline.

If necessary, the pharmaceutical preparations can be sterilized and/or contain adjuvant substances such as preserving, stabilizing, wetting or emulsifying agents, salts for the variation of the osmotic pressure or substances acting as buffers.

The compounds of the present invention can be conveniently administered by the parenteral route preferably intravenously with a dosage in the range of about 1 mg. to 50 mg. per administration.

Also equivalent to the aforesaid β-endorphin analogs for the purposes of this invention are the pharmaceutically acceptable acid addition salts thereof. Such acid addition salts can be dreived from a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic and related acids.

The following Examples serve to further illustrate the present invention.

EXAMPLE 1

Synthesis

The four peptides [Phe$^{27}$, Gly$^{31}$] - $β_h$-EP (I), [Ala$^{6,7}$, Phe$^{27}$, Gly$^{31}$] - $β_h$-EP (II), [Nle$^5$, Phe$^{27}$, Gly$^{31}$] - $β_h$-EP (III), and [D-Thr$^2$, Phe$^{27}$, Gly$^{31}$] - $β_h$EP (IV) were synthesized by improved procedures of the solid-phase method well known in the art.

Protected peptide resins corresponding to peptides I–IV

Boc-glycyl copolystyrene-divinylbenzene resin (1.51 g, 0.60 mmol glycine) was subjected to the following reaction procedure: (1) washing with methylene chloride, 4 × 20 ml; (2) washing with 55% trifluoroacetic acid/methylene chloride, 1 × 20 ml; (3) reaction with 55% trifluoroacetic acid/methylene chloride, 20 ml for 15 min; (4) washing with methylene chloride 2 × 20 ml; (5) washing with dioxane-methylene chloride (1:2), 3 × 20 ml; (6) repeat step 4; (7) reaction with 5% diisopropylethylamine/methylene chloride, 20 ml for 2 min; (8) repeat step 4; (9) repeat step 7; (10) washing with methylene chloride, 5 × 20 ml; (11) reaction with 1.8 mmol of the preformed symmetrical anhydride of the Boc-amino acid in 13 ml of methylene chloride for 20 min; (12) addition of 0.3 mmol of N-methylmorpholine in 2 ml of methylene chloride to the above reaction mixture and continued shaking for 20 min; (13) washing with methylene chloride, 3 × 20 ml; (14) washing with ethanol-methylene chloride (1:2), 3 × 20 ml.

N$^α$-protection for all amino acids was by the Boc group and side-chain protection was as follows : Ser, O-benzyl; Thr, O-benzyl; Glu, γ-benzyl ester; Lys, N$^ε$-o-bromobenzyloxycarbonyl; Tyr, O-benzyloxycarbonyl. The preformed symmetrical anhydrides of the Boc-amino acids were prepared as described by Blake and Li, Int. J. Pept. Prot. Res. 7, 495 (1975) and Boc-asparagine was coupled to the peptide resin in the presence of 1-hydroxybenzotriazole as reported in that reference.

After coupling of the γ-benzyl glutamic acid residue corresponding to position 8 in the β-EP sequence, the peptide resin was dried to yield 3.29 g of protected peptide resin. A one-fifth portion (ca. 600 mg, 0.12 mmol peptide) of the peptide resin was submitted to the above reaction procedure and the final seven amino acid residues were coupled. At the reduced scale, solvent wash volumes were 10 ml and coupling was effected by reaction of the peptide resin with 0.5 mmol of symmetrical anhydride in 6.5 ml of methylene chloride. After coupling of the final amino acid residue the peptide resin was subjected to steps 1–8, washed with ethanol, and dried.

Isolation of peptides I–IV

The same procedure was used to isolate each peptide from the corresponding peptide resin and the details for the isolation of peptide I are typical. The peptide resin (302 mg, 0.060 mmol) was treated with 1 ml of anisole and 8 ml of liquid HF for 1 h at 0°. The HF was evaporated at 0°, 40 ml of cold ethyl acetate was added to the peptide-resin residue, and the resultant mixture was stirred for 10 min at room temperature. The mixture was filtered, and the precipitate was washed with ethyl acetate and air dried. Peptide was extracted from the precipitate by stirring with 6 ml of 0.5 N acetic acid. Filtration gave a filtrate that was chromatographed on Sephadex G-10; material corresponding to the major peak was isolated by lyophilization to give 97 mg of crude peptide I. Chromatography on carboxymethyl-cellulose was previously described by Li et al., Biochem, Biophys. Res. Commun. 71, 19 (1976) gave 41.2 mg of peptide I. Further purification was achieved by partition chromatography on Sephadex G-50 (column: 1.9 × 44 cm) in the system n-butanol: pyridine: 0.1% acetic acid (5:3:11). Material corresponding to the major peak at $R_f$ 0.23 was combined, diluted with an equal volume of water, and evaporate in vacuo to a volume of ca. 10 ml. The concentrated solution was lyophilized and the residue was redissolved in dilute acetic acid and relyophilized to give 29.2 mg of peptide I (14.4% yield based on starting Boc-glycyl resin). Peptides II, III, and IV were isolated in yields of 10, 28, and 21%, respectively.

Paper electrophoresis of peptide I at pH 3.7 and 6.7 (400 V, 3.5 h) have a single ninhydrin positive, chlorine positive spot at $R_f^{lys}$ 0.56 and 0.38, respectively. Thin layer chromatography on silica gel in the system n-butanol:pyridine:acetic acid:water (5:5:1:4) gave a single ninhydrin, chlorine positive spot at $R_f$ 0.51. For enzymatic digestion, a solution of 0.7 mg of peptide plus 14 μg of chymotrypsin and 14 μg of trypsin in 0.15 ml of Tris buffer (pH 8.5, 0.01 M $Mg^{+2}$) was incubated at 37° for 24 h. Then the solution was heated in boiling water for 15 min, cooled to room temperature, and further incubated at 37° with 28 μg of leucineaminopeptidase for 44 h. A portion of the enzyme digest was submitted to the amino acid analyzer and the results are shown in Table 1 together with the amino acid analyses of acid hydrolysates of peptides I–IV.

Table 1

| Amino acid | Peptide I | | Peptide II | | Peptide III | | Peptide IV | |
|---|---|---|---|---|---|---|---|---|
| | Acid[a] | Enzyme[b] | Acid | Enzyme | Acid | Enzyme | Acid | Enzyme |
| Lys | 4.9 (5)[c] | 4.6(5) | 4.7(5) | 4.7(5) | 5.1(5) | 5.1(5) | 5.1(5) | 5.1(5) |
| Asp | 2.1(2) | — | 2.1(2) | — | 2.0(2) | — | 2.1(2) | — |
| Asn | — | | — | | — | | — | |
| Gln | — | 7.7(8)[d] | — | 5.6(6)[d] | — | 7.9(8)[d] | — | 7.7(9)[d] |
| Thr | 3.0(3) | | 1.9(2) | | 2.8(3) | | 3.7(4) | |
| Ser | 1.9(2) | | 0.9(1) | | 1.9(2) | | 1.9(2) | |
| Glu | 2.1(2) | 1.1(1) | 2.1(2) | 1.1(1) | 2.0(2) | 1.0(1) | 2.1(2) | 1.1(1) |
| Pro | 0.9(1) | 1.0(1) | 1.0(1) | 0.9(1) | 1.0(1) | 1.0(1) | 0.9(1) | 0.9(1) |
| Gly | 4.3(4) | 3.7(4) | 4.2(4) | 3.9(4) | 3.8(4) | 3.6(4) | 3.0(3) | 1.9(3) |
| Ala | 2.0(2) | 1.9(2) | 3.9(4) | 3.9(4) | 2.0(2) | 1.9(2) | 2.0(2) | 2.0(2) |
| Val | 0.9(1) | 1.1(1) | 1.0(1) | 1.2(1) | 1.0(1) | 0.9(1) | 1.0(1) | 1.1(1) |
| Met | 1.0(1) | 1.1(1) | 1.1(1) | 1.0(1) | — | — | 1.0(1) | 1.0(1) |
| Ile | 1.3(2) | 1.9(2) | 1.3(2) | 2.0(2) | 1.2(2) | 1.8(2) | 1.1(2) | 1.8(2) |
| Leu | 2.0(2) | 2.1(2) | 2.1(2) | 2.2(2) | 1.9(2) | 2.0(2) | 2.9(2) | 2.3(2) |
| Nle | — | — | — | — | 1.0(1) | 1.0(1) | — | — |
| Tyr | 1.0(1) | 1.0(1) | 1.0(1) | 1.1(1) | 1.0(1) | 1.0(10 | 1.0(1) | 1.0(1) |
| Phe | 2.9(3) | 3.0(3) | 3.0(3) | 3.0(3) | 3.0(3) | 2.8(3) | 3.1(3) | 2.2(3) |

[a]Hydrolysis with constant boiling HCl; 22 h at 110°.
[b]See Experimental section.
[c]Numbers in parentheses are the expected values.
[d]Corresponds to sum of Asn+Gln+Thr+Ser.

EXAMPLE 2

Bioassay

In vitro assay of opiate activity was by the guinea pig ileum method of Kosterlitz et al, Brit. J. Pharmacol. 39, 398 (1970) and in vivo assay in mice was by the tail-flick method of D'Amour and Smith, J. Pharmacol. Exp. Therap. 72, 74 (1941). The experimental procedure and method of calculation has been outlined by Loh et al. Proc. Natl. Acad. Sci. 73, 2895 (1976) and Tseng et al.. Nature 263, 239 (1976).

The opiate activities of peptides I–IV as assayed by the in vitro and in vivo procedures are summarized in Tables 2 and 3.

Table 2

Opiate Activity of Synthetic β-Endorphin Analogs by Guinea Pig Ileum Assay

| Preparations | $IC_{50}$ mol/l | Relative potency[a] |
|---|---|---|
| $β_h$-endorphin ($β_h$-EP) | 4.5 × $10^{-8}$ | 100 |
| [Phe[27],Gly[31]]-$β_h$-EP (I) | 3.5 × $10^{-8}$ | 128 |
| [Ala[6,7],Phe[27],Gly[31]]-$β_h$-EP (II) | 3.8 × $10^{-8}$ | 118 |
| [Nle[5],Phe[27],Gly[31]]-$β_h$-EP (III) | 3.8 × $10^{-8}$ | 118 |
| [D-Thr[2],Phe[27],Gly[31]]-$β_h$-EP (IV) | 3.3 × $10^{-8}$ | 136 |

[a]Relative potencies are calculated using the $IC_{50}$ of $β_h$-endorphin as 100%.

Table 3

| Preparation | intracerebroventricular | | intravenous | |
|---|---|---|---|---|
| | AD$_{50}$ μg/mouse | relative potency | AD$_{50}$ mg/kg | relative potency |
| $\beta_h$-endorphin | 0.11(0.07–0.17) | 100 | 11.4(6.4–19.6) | 100 |
| [Phe$^{27}$,Gly$^{31}$]-$\beta_h$-EP (I) | 0.09(0.08–0.11) | 119 | 7.5(3.4–16.5) | 148 |
| [Ala$^{6,7}$,Phe$^{27}$,Gly$^{31}$]-$\beta_h$-EP (II) | 0.46(0.28–0.77) | 23 | 22.1(14.3–34.3) | 49 |
| [Nle$^5$,Phe$^{27}$,Gly$^{31}$]-$\beta_h$-EP (III) | 0.31(0.14–0.72) | 35 | ca. 17.0 | 65 |
| [D-Thr$^2$,Phe$^{27}$,Gly$^{31}$]-$\beta_h$-EP (IV) | 0.52(0.24–1.16) | 21 | ca. 32.0 | 32 |

$^a$Numbers in parentheses are the 95% confidence limits.
$^b$Relative potencies are calculated on a molar basis using the AD$_{50}$ of $\beta_h$-endorphin as 100%.

It may be noted that there is little correlation between the in vitro assay by the guinea pig ileum method and the in vivo assay in mice by either intravenous (iv) or intracerebroventricular (icv) administration. All of the synthetic analogs are slightly more potent than $\beta_h$-endorphin by the guinea pig ileum assay but, with the exception of peptide I, are significantly less potent in the mouse. The analgesic activity followed iv injection of peptide I is shown in FIG. 2. The duration of analgesic activity after iv injection appeared to be shorter than after icv injection. Peptide I appears to be the first synthetic analog of $\beta_h$-endorphin with the full sequence to possess a greater in vivo analgesic activity than the natural peptide.

I claim:

1. Analogs of $\beta$-human endorphin of the formula

[X, Phe$^{27}$, Gly$^{31}$] - $\beta_h$-endorphin wherein X is selected from null, Ala$^{6,7}$, Nle$^5$ and D-Thr$^2$ and the pharmaceutically acceptable acid addition salts thereof.

2. The compound of claim 1 which is [Phe$^{27}$, Gly$^{31}$] - $\beta_h$-endorphin.

3. The compound of claim 1 which is [Ala$^{6,7}$, Phe$^{27}$, Gly$^{31}$] - $\beta_h$-endorphin.

4. The compound of claim 1 which is [Nle$^5$, Phe$^{27}$, Gly$^{31}$] - $\beta_h$-endorphin.

5. The compound of claim 1 which is [D-Thr$^2$, Phe$^{27}$, Gly$^{31}$] - $\beta_h$-endorphin.